United States Patent [19]

Steiner et al.

[11] 4,447,610

[45] May 8, 1984

[54] 10-SUBSTITUTED 5-CYANOMETHYLENE-DIBENZO[a,d]-CYCLOHEPTENES, THEIR PREPARATIONS, AND THERAPEUTIC AGENTS CONTAINING THESE COMPOUNDS

[75] Inventors: Gerd Steiner, Kirchheim; Hans P. Hofmann, Ludwigshafen; Horst Kreiskott, Wachenheim; Hans-Juergen Teschendorf; Dieter Lenke, both of Ludwigshafen, all of Fed. Rep. of Germany

[73] Assignee: BASF Aktiengesellschaft, Fed. Rep. of Germany

[21] Appl. No.: 237,962

[22] Filed: Feb. 25, 1981

[30] Foreign Application Priority Data

Mar. 8, 1980 [DE] Fed. Rep. of Germany ....... 3009034

[51] Int. Cl.³ ................. C07D 295/14; C07D 223/02; C07D 211/34
[52] U.S. Cl. .................................. 544/381; 546/203; 260/239 BC; 424/250; 424/244; 424/267
[58] Field of Search ................. 544/381; 260/239 BC; 546/203

[56] References Cited

U.S. PATENT DOCUMENTS

| | | | |
|---|---|---|---|
| 3,459,745 | 8/1969 | Fouche | 544/381 |
| 3,459,806 | 8/1969 | Frey et al. | 544/381 |
| 3,496,173 | 2/1970 | Fouche | 424/248 X |
| 3,846,431 | 11/1974 | Edenhotor | 544/381 |

FOREIGN PATENT DOCUMENTS

| | | |
|---|---|---|
| 1000701 | 11/1976 | Canada . |
| 1568089 | 1/1970 | Fed. Rep. of Germany . |
| 1620155 | 1/1970 | Fed. Rep. of Germany . |
| 1620151 | 7/1971 | Fed. Rep. of Germany . |
| 1129029 | 2/1968 | United Kingdom . |

OTHER PUBLICATIONS

Davis, et al. J. Med. Chem., 6, pp. 251-255 (1963).
J. Schmutz, Arzneimittelforschung (Drug Research) 25, (1975), pp. 712-720.

Primary Examiner—Paul M. Coughlan, Jr.
Assistant Examiner—D. B. Springer
Attorney, Agent, or Firm—Keil & Witherspoon

[57] ABSTRACT

10-Substituted 5-cyanomethylene-dibenzo[a,d]-cycloheptenes, their pure cis- and trans-isomers, their N-oxides and their pharmaceutically tolerated addition salts with acids, processes for their preparation, therapeutic agents containing these compounds and their use as drugs, especially as sedatives, hypnotics or tranquilizers.

15 Claims, No Drawings

10-SUBSTITUTED 5-CYANOMETHYLENE-DIBENZO[a,d]-CYCLOHEPTENES, THEIR PREPARATIONS, AND THERAPEUTIC AGENTS CONTAINING THESE COMPOUNDS

The present invention relates to 10-substituted 5-cyanomethylene-dibenzo[a,d]-cycloheptanes, their pure cis- and trans-isomers, their N-oxides and their pharmaceutically tolerated addition salts with acids, processes for their preparation, therapeutic agents containing these compounds, and their use as drugs, especially as sedatives, hypnotics or tranquilizers.

It is known that tricyclic ring systems with a dibenzo structure and a central heterocyclic 7-membered ring, which may or may not possess a basic branch, for example an N-methylpiperazine radical, can exhibit neuroleptic effects. Examples of such tricyclic compounds are N-methylpiperazine derivatives of dibenzo[b,e][1,4]-diazepines (clozapine), dibenzo[b,f][1,4]-thiazepines (clotiapine), dibenzo[b,f][1,4]-oxazepines (loxapine) or morphantridines (perlapine), as described, for example, in the review by J. Schmutz in Arzneimittelforschung 25 (1975), 712-720.

German patent application No. P 2,918,778.8 proposes 6-substituted 11-alkylene-morphanthridines having valuable pharmacological properties. The application in question concerns derivatives having a modified ring system and exhibiting a different pattern of pharmacological effects.

We have found that 10-substituted 5-cyanomethylene-dibenzo[a,d]-cycloheptenes of the general formula I

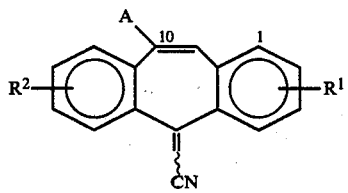

I where $R^1$ and $R^2$ are hydrogen, halogen, especially fluorine, chlorine or bromine, alkyl of 1 to 3 carbon atoms or trifluoromethyl, and A is an alkoxy radical —O—$R^3$, where $R^3$ is alkyl of 1 to 3 carbon atoms, or cycloalkyl or cycloalkylmethylene of 3 to 6 carbon atoms in the ring, which ring may or may not contain a nitrogen atom which may or may not be substituted by alkyl of 1 to 3 carbon atoms and may or may not be in the form of an N-oxide, or $R^3$ is aminoalkyl of 2 to 7 carbon atoms, the amine nitrogen being unsubstituted or substituted by alkyl of 1 to 5 carbon atoms or being a member of a 5-membered, 6-membered or 7-membered saturated ring which may or may not contain a nitrogen or an oxygen as a further hetero-atom and in which an additional nitrogen may be substituted by alkyl of 1 to 3 carbon atoms and may or may not be in the form of an N-oxide, or A is an amino radical —$NR^4R^5$, where $R^4$ and $R^5$ are identical or different and each is hydrogen, alkyl of 1 to 5 carbon atoms, cycloalkyl or cycloalkylmethylene of 3 to 6 carbon atoms in the ring, which ring may or may not contain a nitrogen atom which may or may not be substituted by alkyl of 1 to 3 carbon atoms and may or may not be in the form of an N-oxide, hydroxyalkyl of 2 to 5 carbon atoms or aminoalkyl of 2 to 7 carbon atoms, the amine nitrogen being unsubstituted or substituted by lower alkyl of 1 to 5 carbon atoms, by aralkyl of 7 to 9 carbon atoms or by phenyl, or being a member of a 5-membered, 6-membered or 7-membered saturated ring which may or may not contain a nitrogen or an oxygen as a further hetero-atom and in which a nitrogen present is substituted by lower alkyl of 1 to 3 carbon atoms or by hydroxyalkyl of 2 or 3 carbon atoms, or is alkenyl of 2 to 5 carbon atoms, or $R^4$ and $R^5$ together with the nitrogen atom by which they are linked are a 5-, 6- or 7-membered saturated ring, which may or may not contain a nitrogen or an oxygen as a further hetero-atom, an additional nitrogen atom being unsubstituted or substituted by alkyl of 1 to 3 carbon atoms, hydroxyalkyl of 2 or 3 carbon atoms, alkoxyalkyl, the alkoxy and alkyl radical each being of 1 to 3 carbon atoms, cycloalkyl or cycloalkylmethyl, of 3 to 7 carbon atoms in the cycloalkyl ring, or alkynyl of 2 to 5 carbon atoms, and being additionally, where appropriate, substituted by oxygen in the form of an N-oxide, and their physiologically tolerated addition salts with acids, exhibit valuable pharmacological properties.

Important meanings of $R^1$ and $R^2$ include hydrogen, fluorine, chlorine, methyl and trifluoromethyl, amongst which hydrogen and chlorine are particularly preferred.

Where A is alkoxy —$OR^3$, important meanings of $R^3$ are 2-dimethylamino-ethyl, 3-dimethylamino-propyl, piperidin-1-yl-ethyl, N-methyl-piperidin-3-yl-methyl, N-methyl-piperidin-2-yl-methyl, N-methyl-piperidin-4-yl and N-methyl-N-oxy-piperidin-3-yl-methyl, amongst which N-methyl-piperidin-3-yl-methyl, N-methyl-N-oxy-piperidin-3-yl-methyl and 2-dimethylamino-ethyl are particularly preferred.

Examples of amine radicals A, ie.

where one of $R^4$ or $R^5$ is hydrogen, are: 2-aminoethyl, 2-dimethylamino-ethyl, 3-dimethylamino-propyl, 2-hydroxyethyl, 2-piperidin-1-yl-ethyl, 2-pyrrolidin-1-yl-ethyl, 3-piperidin-1-yl-propyl, N-ethyl-pyrrolidin-2-yl-methyl, 2-morpholin-1-yl-ethyl, 2-piperazin-1-yl-ethyl, N-methyl-piperidin-3-yl-methyl, N-methyl-N-oxy-piperidin-3-yl-methyl, N-methyl-piperidin-2-yl-methyl, 1-methyl-2-morpholin-1-yl-ethyl, 2-(4-methyl-piperazin-1-yl)-ethyl, 3-(4-methyl-piperazin-1-yl)-propyl, 2-(N-methyl-N-benzyl-amino)-ethyl, 3-(N-methyl-N-benzyl-amino)-propyl, 1-methyl-2-(4-methyl-piperazin-1-yl)-ethyl and N-methyl-piperidin-4-yl.

Examples of amine radicals A, ie. —$NR^4R^5$, where $R^4$ and $R^5$ form a 5-membered, 6-membered or 7-membered saturated ring, which may or may not contain a nitrogen or an oxygen as a further hetero-atom, are piperazinyl, homopiperazinyl, piperidinyl and morpholinyl radicals.

Particularly preferred radicals —$NR^4R^5$ are 4-methyl-piperazinyl, 4-methyl-4-oxy-piperazinyl, 4-cyclopropyl-piperazinyl, 4-cyclopropylmethyl-piperazinyl, 4-propyn-2-yl-piperazinyl, 4-(2-hydroxy)-ethyl-piperazinyl, 4-ethyl-piperazinyl and N-methyl-homopiperazinyl, as well as radicals —$NHR^4$, where $R^4$ is 2-dimethylaminoethyl or 2-piperidin-1-yl-ethyl.

It is to be noted that the novel compounds of the formula I exist as cis-trans isomers Ia and Ib.

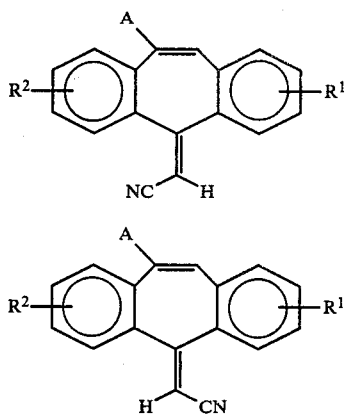

If desired, the cis-trans isomers can be separated, for example by fractional crystallization or by column chromatography. The structure of the individual isomers can for example by allocated on the basis of X-ray structural analysis, as shown in the Examples.

In accordance with the above meanings, the following compounds may be mentioned as being particularly preferred and active: cis,trans-5-cyanomethylene-10-(4-methyl-piperazin-1-yl)-dibenzo[a,d]-cycloheptene, cis-5-cyanomethylene-10-(4-methyl-piperazin-1-yl)-dibenzo[a,d]-cycloheptane, trans-5-cyanomethylene-10-(4-methyl-piperazin-1-yl)-dibenzo[a,d]-cycloheptene, cis,-trans-5-cyanomethylene-10-(4-methyl-4-oxy-piperazin-1-yl)-dibenzo[a,d]-cycloheptene, cis-5-cyanomethylene-10-(4-methyl-4-oxy-piperazin-1-yl)-dibenzo[a,d]-cycloheptene, trans-5-cyanomethylene-10-(4-methyl-4-oxypiperazin-1-yl)-dibenzo[a,d]-cycloheptane, cis,trans-5-cyanomethylene-2-chloro-10-(4-methyl-piperazin-1-yl)-dibenzo[a,d]-cycloheptane, cis-5-cyanomethylene-2-chloro-10-(4-methyl-piperazin-1-yl)-dibenzo[a,d]-cycloheptene, trans-5-cyanomethylene-2-chloro-10-(4-methyl-piperazin-1-yl)-dibenzo[a,d]-cycloheptene, cis,-trans-5-cyanomethylene-10-(4-ethyl-piperazin-1-yl)-dibenzo[a,d]-cycloheptene, cis-5-cyanomethylene-10-(4-ethyl-piperazin-1-yl)-dibenzo[a,d]-cycloheptene, trans-5-cyanomethylene-10-(4-ethyl-piperazin-1-yl)-dibenzo-[a,d]-cycloheptene, cis,trans-5-cyanomethylene-10-(N'-methyl-homopiperazin-1-yl)-dibenzo[a,d]-cycloheptene and cis,trans-5-cyanomethylene-10-(4-$\beta'$-hydroxyethylpiperazin-1-yl)-dibenzo[a,d]-cycloheptene.

As the Examples show, the separation into the cis-isomer and trans-isomer can, in individual cases, be carried out without excessive expense.

The novel compounds of the formula I are prepared by reacting a compound of the formula II

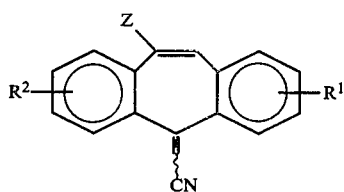

where $R^1$ and $R^2$ have the meanings given for formula I, or the preferred meanings, and Z is a nucleofugic leaving group, with a nucleophilic agent AH, where A has the meanings given for formula I, and, if desired, converting the resulting compound to the N-oxide and/or to an addition salt with a physiologically tolerated acid.

Suitable nucleofugic leaving groups Z are halogen, especially bromine and chlorine.

The reactions is advantageously carried out in the presence of an excess of the amine or alcohol corresponding to the formula AH, which compound may or may not at the same time serve as a solvent and may or may not serve as an acid acceptor, and in the presence of from 1 to 2 mole equivalents of potassium tert.-butylate. Where appropriate, the reaction can be carried out in the presence of an inert solvent, such as a cyclic saturated ether, especially tetrahydrofuran or dioxane, benzene or a benzene hydrocarbon, eg. xylene, mesitylene or decahydronaphthalene. The reaction is as a rule carried out at from room temperature to 150° C. and is in general complete within 3–10 hours. In some cases, it may be advantageous to exclude atmospheric oxygen and carry out the reaction under an inert gas, for example under nitrogen.

In the reactions, the nucleophilic agent AH is advantageously used in not less than 2-molar, and up to 20-molar, excess.

The conversion of a compound of the formula I to its N-oxide is carried out in a conventional manner, advantageously with aqueous (30% strength by weight) hydrogen peroxide in ethanol solution. The conversion of the compound to its addition salt with a physiologically tolerated acid is also carried out in a conventional manner.

The starting compounds of the formula II are prepared by carbonyl olefination, wherein 10-bromo-(chloro)-dibenzo[a,d]-cyclohepten-5-one of the formula

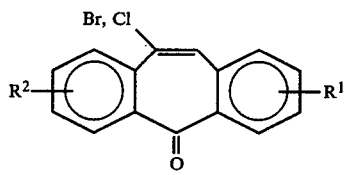

where $R^1$ and $R^2$ have the meanings given for formula I, is reacted with a phosphonate of the formula IVa

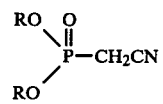

where R is alkyl of 1 to 3 carbon atoms, under the conditions of a Wittig-Horner reaction, in an inert solvent—dimethylformamide being particularly preferred—in the presence of one mole equivalent of a base, preferably a sodium alcoholate, sodium hydride or sodium amide, at from 20° to 80° C., or is reacted with a phosphonium salt of the formula IVb

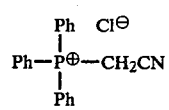

where Ph is a phenyl radical, under the conditions of a classical Wittig reaction, in an aprotic organic solvent, especially a saturated aliphatic or saturated cyclic ether, eg. diethyl ether, tetrahydrofuran or dioxane, or, preferably, in dimethylformamide, in the presence of one mole equivalent of a base, especially of an alkali metal alcoholate, preferably sodium methylate or sodium ethylate, or sodium hydride or sodium amide, or of an organo-metallic compound, such as butyl-lithium, at from 20° to 100° C.

In the above reactions, the sequence of carbonyl olefination and introduction of the nucleophilic radical A into the 10-position can be successfully inverted. In that case, the corresponding 10-bromo-dibenzo[a,d]-cyclohepten-5-one is used as the starting material and is reacted with a nucleophilic agent AH to give the 10-substituted dibenzo[a,d]-cycloheptene derivative of the formula V

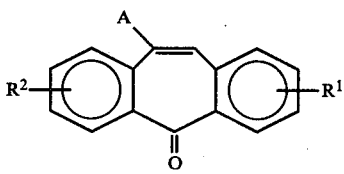

The carbonyl olefination is then carried out as described above.

The 10-bromo(chloro)-dibenzo[a,d]-cyclohepten-5-ones of the general formula III are in some cases known from the literature (W. Treibs and H. J. Klinkhammer, Ber. 84 (1951), 671; H. L. Slates and N. L. Wendler, U.S. Pat. No. 3,297,763); if not previously known, they can be prepared from the corresponding dibenzosuberone derivatives (cf. E. L. Engelhardt et al., J. Med. Chem. 8 (1965), 829), by double bromination with N-bromosuccinimide, followed by elimination of hydrogen bromide by means of methanolic potassium hydroxide solution (cf. E. Waldvogel et al., Helv. Chim. Acta 59 (1976), 866).

In addition to the compounds referred to in the Examples, the following compounds may be mentioned by way of illustration: cis,trans-8-chloro-5-cyanomethylene-10-(4-methyl-piperazin-1-yl)-dibenzo[a,d]-cycloheptene, cis,trans-2-fluoro-5-cyanomethylene-10-(4-methyl-piperazin-1-yl)-dibenzo[a,d]-cycloheptene, cis,trans-8-fluoro-5-cyanomethylene-10-(4-methylpiperazin-1-yl)-dibenzo[a,d]-cycloheptane, cis,trans-2-trifluoromethyl-5-cyanomethylene-10-(4-methyl-piperazin-1-yl)-dibenzo[a,d]-cycloheptene, cis,trans-8-trifluoromethyl-5-cyanomethylene-10-(4-methyl-piperazin-1-yl)-dibenzo[a,d]-cycloheptene, cis,trans-5-cyanomethylene-10-(4-cyclopropyl-piperazin-1-yl)-dibenzo[a,d]-cycloheptene, cis,trans-5-cyanomethylene-10-(4-cyclopropylmethyl-piperazin-1-yl)-dibenzo[a,d]-cycloheptene and cis,trans-5-cyanomethylene-10-(4-propyn-2-yl-piperazin-1-yl)-dibenzo[a,d]-cycloheptene.

The compounds according to the invention, of the formula I, are as a rule obtained in the form of yellowish or yellow crystals, and can be recrystallized from the conventional organic solvents, preferably from a lower alcohol, such as ethanol, or be purified by column chromatography.

Where necessary, the compounds can be separated into the cis-isomer and trans-isomer by fractional crystallization in a chlorohydrocarbon, preferably methylene chloride, a lower monohydric alcohol, preferably methanol or ethanol, or a saturated cycloaliphatic hydrocarbon, preferably cyclohexane, or by column chromatography, especially over silica gel, using methylene chloride, or a mixture of methylene chloride and methanol in the volume ratio of from 99:1 to 85:15.

The free 10-substituted 5-cyanomethylenedibenzo[a,d]-cycloheptenes of the formula I can be converted to an addition salt with a pharmacologically tolerated acid in a conventional manner, preferably by adding one equivalent of the corresponding acid to the solution. Examples of suitable conventional physiologically tolerated acids are, amongst inorganic acids, hydrochloric acid, hydrobromic acid, phosphoric acid and sulfuric acid, and, amongst organic acids, oxalic acid, maleic acid, fumaric acid, lactic acid, tartaric acid, malic acid, citric acid, salicylic acid, adipic acid and benzoic acid; other acids are listed in Fortschritte der Arzneimittelforschung, published by Birkhäuser, Basel and Stuttgart, 10 (1966), 224–225.

The compounds according to the invention possess valuable pharmacological properties. They may be used as sedatives, hypnotics, tranquilizers, neuroleptics or antidepressants. Any one compound according to the invention may exhibit several of the above types of effect in combination. In some cases, an individual pure isomer, obtained after isomer separation, may preferentially exhibit a particular effect.

According to the results of the pharmacological experiments we have carried out, the compounds according to the invention are, by virtue of their sedative-tranquilizing, muscle-relaxing and antimonaminergic effect, particularly suitable for use as sedatives, hypnotics and minor or major tranquilizers.

The following methods were used to analyze the action of the compounds:

1. Sedative action

4–8 groups of 3 female NMRI mice are given the compound orally. The orientation hypermotility induced by a new environment is determined photoelectrically, 30 minutes after administration of the compound, for a period of 30 minutes.

The ED50% is the dose which produces a decrease in orientation hypermotility by 50%, compared to control animals treated with placebo.

2. Muscle-relaxing action

The measurement is based on quantifying the tonic extensor reflex on the rabbit gastrocnemius (Teschendorf et al., Arch. Pharmacol. exp. Path. 266 (1970), 462). The rabbit is fixed in a special apparatus which permits bending the paw at the talocalcanean joint in a defined and reproducible manner. As a result of this bending, a tonic extensor reflex is triggered in the thigh muscle. The electrical activity of the muscle during contraction is registered and the individual pulses are counted. The extension (duration 5 s) is repeated at intervals of one minute. After a constant number of pulses has been reached (constituting the control value), the test substance is administered intravenously. The number of pulses after administration is related to the previous value. For each dose investigated, 4–6 animals are used. The ED 50% is the dose which reduces the muscle activity to half, based on the initial value.

3. Antitryptamine action

Tryptamine.HCl (16 mg/kg administered intravenously) regularly causes the following symptoms in rats: clonic front paw movements, back-arching and retropulsion, as well as mandibular movements (Tedeschi et al., J. Pharmacol. Exp. Ther. 126 (1959), 223).

The test substances are administered intraperitoneally 30 minutes before the tryptamine. The criterion of whether a compound has an effect is whether the front paw movements remain absent over 5 minutes' observation after the injection of tryptamine.

The mean inhibitory dose (ED 50%) is determined, by means of Probit analysis, as the dose which prevents the symptom in half the animals.

4. Anticholinergic action

Groups of 10 female NMRI mice are given physostigmine subcutaneously, at a lethal dose (0.825 mg/kg). The test substances are administered orally 30 minutes before the administration of physostigmine.

The ED 50% is determined as the dose of compound which protects 50% of the animals against death from physostigmine.

5. Acute toxicity

Groups of 5-10 female NMRI mice are given the compounds intraperitoneally. The LD 50 is determined as the dose after which 50% of the treated animals die.

In these experiments (cf. Table 1) remarkably great sedative-hypnotic effects of the compounds according to the invention were demonstrated. The effects are at least as pronounced as in the case of the reference compounds clozapine and perlapine, and in some cases substantially (up to 10 times) greater. The compounds furthermore exhibit very pronounced muscle-relaxing properties. In this respect they are superior to the reference substances by up to a factor of 100. These types of effect are shown by cis-trans mixtures, but are particularly pronounced in the cis-compounds of Examples 1a and 4a.

The antimonoaminergic action, measured in the present case in terms of the tryptamine antagonism—may be regarded as a parameter of the neuroleptic quality. In this test, again, distinct effects were found, which in some cases were somewhat less pronounced than for the reference substances, but on the other hand were markedly more pronounced in the case of the compound of Example 4a.

In contrast to clozapine, the novel compounds show no anticholinergic properties, as demonstrated by the antiphysostigmine test on mice, from which it may be concluded that the peripheral side-effects on therapeutic use are less.

On the basis of the pharmacological findings, the novel compounds can in particular be used, in appropriate pharmaceutical formulations, as sedatives, hypnotics, minor tranquilizers or major tranquilizers.

mula I, or a pharmacologically tolerated addition salt thereof with an acid, as the active compound.

Therapeutic agents containing conventional carriers or diluents and the conventionally used technical auxiliaries can be prepared in a conventional manner, in accordance with the desired route of administration and employing a unit dosage suitable for the particular application. A suitable individual dose in man is from 10 to 100 mg.

The novel compounds may be employed in the conventional solid or liquid pharmaceutical forms, such as tablets, capsules, powders, granules, dragees or solutions. These are prepared in a conventional manner, and to do so the active compounds can be mixed with the conventional pharmaceutical auxiliaries, such as talc, gum arabic, sucrose, lactose, cereal starch or corn starch, potato flour, magnesium stearate, alginates, gum tragacanth, carraghenates, polyvinyl alcohol, polyvinylpyrrolidone, aqueous or non-aqueous carriers, wetting agents, dispersants, emulsifiers and/or preservatives (cf. L. G. Goodman and A. Gilman, The Pharmacological Basis of Therapeutics). The formulations thus obtained normally contain from 0.001 to 99% by weight of the active compound.

The preferred formulations are those suitable for oral administration. Examples of these are tablets, film tablets, dragees, capsules, pills, powders, solutions, suspensions and depot forms. Parenteral formulations, such as injection solutions, may also be used. Suppositories are a further example of suitable formulations.

Appropriate tablets may be obtained, for example, by mixing the active compound with conventional auxiliaries, for example inert diluents, such as dextrose, sugar, sorbitol, mannitol, polyvinylpyrrolidone, calcium carbonate, calcium phosphate or lactose, disintegrating agents, such as corn starch or alginic acid, binders, such as starch or gelatin, lubricants, such as magnesium stearate or talc, and/or agents for achieving a depot effect, such as carboxypolymethylene, carboxymethylcellulose, cellulose acetate phthalate or polyvinyl acetate. The tablets can also consist of a plurality of layers.

Accordingly, dragees can be prepared by coating cores, prepared similarly to the tablets, with agents conventionally used in dragee coatings, for example collidone or shellac, gum arabic, talc, titanium dioxide or sugar. The dragee coating can also consist of a plurality of layers, and the auxiliaries mentioned above in

TABLE 1

| Example No. | Sedative action ED 50% | Sedative action R.A.[1] | Muscle relaxation ED 50% | Muscle relaxation R.A. | Antitryptamine action ED 50% | Antitryptamine action R.A. | Anticholinergic action ED 50% | Toxicity LD 50 |
|---|---|---|---|---|---|---|---|---|
| 1 | 0.96 | 4.94 | 0.0064 | 7.19 | | | >10 | 324 |
| 1a | 0.80 | 5.92 | 0.00085 | 54.12 | 8.6 | 0.58 | >10 | |
| 4 | 2.0 | 2.37 | 0.0046 | 10.00 | | | >21.5 | |
| 4a | 0.44 | 10.77 | 0.0046 | 10.00 | 0.7 | 7.14 | >21.5 | |
| 5 | 1.38 | 3.43 | 0.013 | 3.54 | 18.6 | 0.27 | >21.5 | 287 |
| 5a | 1.0 | 4.74 | 0.01 | 4.60 | 11.2 | 0.45 | >21.5 | >100 |
| 7 | 0.97 | 4.89 | 0.013 | 3.54 | | | >21.5 | >100 |
| 12 | 1.4 | 3.39 | 0.1 | 0.46 | 12.5 | 0.40 | >21.5 | >100 |
| Clozapine | 4.74 | 1.00 | 0.046 | 1.00 | 5.0 | 1.00 | 14.1 | 215 |
| Perlapine | 2.01 | 2.36 | 0.1 | 0.46 | 4.1 | 1.22 | >21.5 | 215 |

[1]R.A. = relative activity

Accordingly, the present invention also relates to a therapeutic agent which in addition to conventional carriers and diluents contains a compound of the formula connection with tablets may be used therein.

Solutions or suspensions containing the novel active compounds may additionally contain flavor improvers, such as vanillin or orange extract. They may also contain suspending agents, such as sodium carboxymethylcellulose, or preservatives, such as p-hydroxybenzoates. Capsules containing the active compounds may be prepared, for example, by mixing the active compound with an inert carrier, such as lactose or sorbitol, and encapsulating the mixture in gelatin capsules. Suitable suppositories can be prepared, for example, by mixing the active compounds with appropriate carriers, such as neutral fats or polyethylene glycol or their derivatives.

The Examples which follow illustrate the invention. The melting points given for the cis-trans isomer mixtures may vary somewhat according to the cis-trans ratio.

EXAMPLE 1 cis- and trans-5-Cyanomethylene-10-(4-methyl-piperazin-1-yl)-dibenzo[a,d]-cycloheptene 20.0 g (65 millimoles) of 10-bromo-5-cyanomethylene-dibenzo[a,d]-cycloheptene (cis,trans-isomer mixture) are suspended in 80 ml of N-methylpiperazine. 8.6 g (84 millimoles) of potassium tert.-butylate are added, a little at a time, whilst stirring, and the reaction mixture is then stirred for a further 10–20 hours at room temperature, under nitrogen. Thereafter it is poured onto ice water and the yellowish crude product is filtered off. It is purified by recrystallization from ethanol or by column chromatography (silica gel, 95/5 methylene chloride/methanol). 17 g (80% yield) of product are isolated as the cis, trans-isomer mixture, melting point 92°–97° C.

To separate the cis-isomer and trans-isomer, the isomer mixture is digested in about 80 ml of boiling methanol and the insoluble constituents are filtered off hot. After washing with a small amount of methanol, 3.2 g of a yellow solid are obtained; according to a thin layer chromatogram (silica gel, mobile phase 85/15 toluene/methanol) this product consists principally of the nonpolar cis-isomer a.

The 2nd fraction which crystallizes after a few hours frequently consists of the isomer mixture. However, from the remaining mother liquor 2.0–2.5 g of greatly enriched polar trans-isomer b can be crystallized; this product is filtered off and washed with a small amount of methanol.

On concentrating the mother liquor, adding the isomer mixture obtained above, taking the material up again in 50 ml of boiling methanol and repeating the above operations several times, further fractions of the greatly enriched geometrical isomers are obtained, and these are subsequently additionally recrystallized from ethanol. cis-Isomer 1a: yellow crystals, of melting point 199°–200° C.; trans-isomer 1b: yellow crystals, of melting point 189°–191° C.

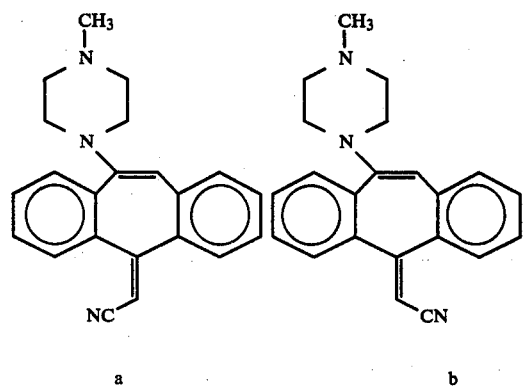

a         b

EXAMPLE 2 cis,trans-10-Bromo-5-cyanomethylene-dibenzo[a,d]-cycloheptene

To prepare the intermediate 10-bromo-5-cyanomethylene-dibenzo[a,d]-cycloheptene, a carbonyl olefination of 10-bromo-dibenzo[a,d]-cyclohepten-5-one is carried out by a Wittig-Horner reaction or by a conventional Wittig synthesis:

30.0 g (105 millimoles) of 10-bromo-dibenzo[a,d]-cyclohepten-5-one are dissolved in 300 ml of warm dimethylformamide and the solution is stirred under nitrogen. 31.8 g (180 millimoles) of diethyl-cyanomethyl-phosphonate and 31.5 g (180 millimoles) of 30% strength sodium ethylate dissolved in 100 ml of dimethylformamide are then slowly and simultaneously added dropwise (an intensification of color, and rise in temperature, indicate the start of the Wittig reaction). After stirring for a further 18 hours at room temperature, the reaction product is poured onto ice water and the solid which precipitates is filtered off. After thorough washing with water, the crude product is dried and recrystallized from ethanol. Yield: 28.5 g (88%) of colorless crystals of melting point 197°–200° C.

Classical Wittig process: triphenyl-cyanomethyl-phosphonium chloride is introduced into dimethylformamide, 1 mole equivalent of a 30% strength sodium methylate solution is then added dropwise, or 1 mole equivalent of sodium hydride is added, and finally 1 mole equivalent of a solution of 10-bromo-dibenzo[a,d]-cyclohepten-5-one in dimethylformamide is introduced. The reaction mixture is stirred for 5–8 hours at 50°–80° C. and is then poured onto ice water and extracted repeatedly with methylene chloride. The organic phase is dried and concentrated and the crude product obtained is recrystallized from ethanol. Yield: 72% of colorless crystals of melting point 198°–201° C.

EXAMPLE 3

10-Bromo-dibenzo[a,d]-cyclohepten-5-one

The 10-bromo-dibenzo[a,d]-cyclohepten-5-ones of the general formula III, used as starting materials for the Wittig reactions, are prepared either by the method of W. Treibs and H. J. Klinkhammer, Ber. 84 (1951), 671 or by the method of E. Waldvogel et al., Helv. Chim. Acta 59 (1976), 866, for example:

(a) 2-Chloro-dibenzosuberone: E. L. Engelhardt et al., J. Med. Chem. 8 (1965), 829.

(b) 2-Chloro-10-bromo-dibenzo[a,d]-cyclohepten-5-one: preparation in accordance with E. Waldvogel, Helv. Chim. Acta 59 (1976), 866, by double bromination with N-bromosuccinimide and subsequent elimination of hydrogen bromide; melting point 127°–129° C.

EXAMPLE 4 cis- and trans-2-Chloro-5-cyanomethylene-10-(4-methylpiperazin-1-yl)-dibenzo[a,d]-cycloheptene The compound is synthesized similarly to Examples 1, 2 and 3, using the corresponding 2-chlorinated derivatives.

An 84% yield of 2-chloro-5-cyanomethylene-10-(4-methyl-piperazin-1-yl)-dibenzo-[a,d]-cycloheptene is isolated as the cis,trans-isomer mixture, of melting point 196°–198° C.

To separate the cis-isomer and trans-isomer, the isomer mixture is digested in a small amount of boiling ethanol and the insoluble constituents are filtered off hot. After washing with a small amount of ethanol, a yellow solid is obtained, which according to a thin layer chromatogram (silica gel, mobile phase 85/15 toluene/methanol) consists principally of the non-polar cis-isomer a.

The fraction which crystallizes after a few hours consists of greatly enriched polar trans-isomer b, which is filtered off and washed with a small amount of ethanol.

Repeating the above operations several times gives further fractions of the greatly enriched geometrical isomers, which are subsequently additionally recrystallized from ethanol. cis-Isomer 4a: yellow crystals of melting point 227°–229° C; trans-isomer 4b: yellow crystals of melting point 223°–225° C.

The X-ray structural analysis carried out on isomer a proves the 2-position of the chlorine atom, as well as the cis-position of the cyanomethylene group relative to the piperazine ring.

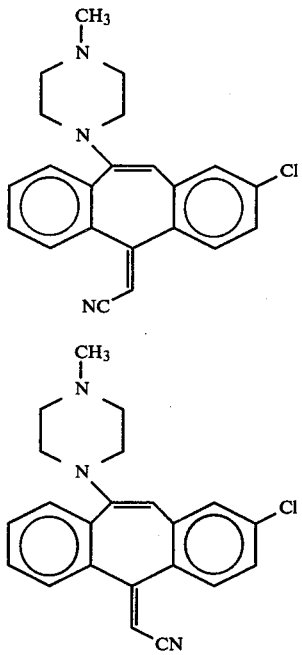

a b

EXAMPLE 5 cis,trans-5-Cyanomethylene-10-(4-ethyl-piperazin-1-yl)-dibenzo[a,d]-cycloheptene The synthesis is carried out similarly to Example 1, using N-ethylpiperazine. After recrystallization from methanol, yellow crystals of melting point 153°–158° C. are obtained.

Fractional crystallization from methanol permits the isolation of the non-polar cis-compound 5a (thin layer chromatogram on silica gel, mobile phase 85/15 toluene/methanol) of melting point 164°–166° C., and of the polar trans-isomer 5b, of melting point 161°–162° C., both in the form of yellow needles.

EXAMPLE 6 cis,trans-5-Cyanomethylene-10-(N'-methyl-homopiperazin-1-yl)-dibenzo[a,d]-cyclohepten.½ $H_2O$ The synthesis is carried out similarly to Example 1, using N-methylhomopiperazine. After purification by column chromatography (silica gel, 95/5 methylene chloride/methanol), yellow crystals of melting point 80°–86° C. are obtained.

EXAMPLE 7 cis,trans-5-Cyanomethylene-10-(N-β-hydroxyethyl-piperazin-1-yl)-dibenzo[a,d]-cycloheptene.½ $H_2O$ The synthesis is carried out similarly to Example 1, using N-β-hydroxyethylpiperazine and increasing the temperature, during the final stirring, to 50° C. for 3 hours. After purification by column chromatography (silica gel, 95/5 methylene chloride/methanol), yellow crystals of melting point 92°–99° C. are obtained.

EXAMPLE 8 cis,trans-5-Cyanomethylene-10-(2-dimethylamino-ethylamino)-dibenzo[a,d]-cycloheptene.½ $H_2O$ The synthesis is carried out similarly to Example 1, using dimethylaminoethylamine.

The crude product is dissolved in methylene chloride and the solution is stirred with active charcoal for 3 hours at room temperature. After working up and drying, orange crystals of melting point 75°–82° C. are obtained.

EXAMPLE 9 cis,trans-5-Cyanomethylene-10-(2-piperidin-1-yl-ethylamino)-dibenzo[a,d]-cycloheptene.½ $H_2O$ The synthesis is carried out similarly to Example 1, using 2-piperidin-1-yl-ethylamine. The crude product is digested in water and the mixture is stirred for 1 hour at room temperature. After filtering off, washing with water and drying, yellowish crystals of melting point 85°–88° C. are obtained.

EXAMPLE 10 cis,trans-5-Cyanomethylene-10-(2-dimethylamino-ethoxy)-dibenzo[a,d]-cycloheptene The synthesis is carried out similarly to Example 1, using dimethylaminoethanol and increasing the temperature, during the final stirring, to 110° C. for 3 hours. After purification by column chromatography (silica gel, 95/5 methylene chloride/methanol), a yellowish oil, which crystallizes slowly, is obtained; melting point: 40°–46° C.

In addition, a by-product is formed, which is identifiable as cis,trans-5-carboxamidomethylene-10-(2-dimethylamino-ethoxy)-dibenzo[a,d]-cycloheptene.

EXAMPLE 11 cis,trans-5-Cyanomethylene-10-(N-methyl-piperidin-3-yl-methoxy)-dibenzo[a,d]-cycloheptene The synthesis is carried out similarly to Example 1, using N-methyl-3-hydroxymethyl-piperidine and increasing the temperature, during the final stirring, to 50° C. for 2 hours. The crude product is filtered off, washed thoroughly with water, purified by digesting for 1 hour with a large amount of water, and filtered off and dried. Yellow crystals of melting point 84°–89° C. are obtained.

EXAMPLE 12 cis,trans-5-Cyanomethylene-10-(4-methyl-4-oxy-piperazin-1-yl)-dibenzo[a,d]-cycloheptene.2½ $H_2O$ 3.0 g (9.2 millimoles) of cis,trans-5-cyanomethylene-10-(4-methyl-piperazin-1-yl)-dibenzo[a,d]-cycloheptene (Example 1) are dissolved in 100 ml of hot ethanol and 5 ml of 30% strength hydrogen peroxide are added. After refluxing the mixture for 5 hours, the excess hydrogen peroxide is destroyed by refluxing for 2 hours in the presence of a small sheet of platinum which is dropped into the reaction mixture. After filtering, the reaction mixture is concentrated and the N-oxide obtained is purified by column chromatography (silica gel, mobile phase 95/5 methylene chloride/methanol). 2.2 g (70%) of yellow crystals of melting point 134°–138° C. are obtained.

EXAMPLE 13

Inversion of the sequence of carbonyl olefination and introduction of the nucleophilic radical A (a) 5.0 g (17.5 millimoles) of 10-bromo-dibenzo[a,d]-cyclohepten-5-one are suspended in 30 ml of N-methyl-piperazine. 4.8 g (47 millimoles) of potassium tertiary butylate are added, a little at a time, with stirring, and the reaction mixture is stirred for 6 hours under nitrogen at 110° C. The excess methylpiperazine is then distilled off under reduced pressure and the residue is partitioned between water and methylene chloride. The organic phase is washed three times with water, dried and concentrated; 4.9 g (92%) of 10-(N-methyl-piperazin-1-yl)-dibenzo[a,d]-cyclohepten-5-one are isolated as an oil, which is sufficiently pure for further conversion.

(b) 3.1 g (10.2 millimoles) of 10-(N-methyl-piperazin-1-yl)-dibenzo[a,d]-cyclohepten-5-one are dissolved in 30 ml of dimethylformamide and the solution is stirred under nitrogen. 2.48 g (14 millimoles) of diethyl-cyanomethyl-phosphonate and 2.45 g (14 millimoles) of 30% strength sodium methylate dissolved in 10 ml of dimethylformamide are then slowly and simultaneously added dropwise (a deepening of color, and rise in temperature, indicate the start of the Wittig reaction). After a further 12 hours' stirring at room temperature, the reaction product is poured onto ice water and the solid which has precipitated is filtered off. After column chromatography (silica gel, 95/5 methylene chloride/methanol), cis,trans-5-cyanomethylene-10-(4-methyl-piperazin-1-yl)-dibenzo[a,d]-cycloheptene is isolated in 67% yield; melting point 91°–95° C.

EXAMPLE 14 cis,trans-5-Cyanomethylene-10-(piperazin-1-yl)-dibenzo-[a,d]-cycloheptene. $H_2O$ The synthesis is carried out similarly to Example 1, using dimethylformamide as the solvent and employing 5 mole equivalents of piperazine. After purification by column chromatography, yellow crystals, of melting point 159°–162° C., are obtained in 75% yield.

Pharmaceutical formulations prepared in a conventional manner:

| Examples of tablets | |
|---|---|
| 1. An active compound of the formula I | 5 mg |
| Lactose | 200 mg |
| Methylcellulose | 15 mg |
| Corn starch | 50 mg |
| Talc | 11 mg |
| Magnesium stearate | 4 mg |
| 2. An active compound of the formula I | 20 mg |
| Lactose | 178 mg |
| Avicel | 80 mg |
| Polywachs 6000 | 20 mg |
| Magnesium stearate | 2 mg |
| 3. An active compound of the formula I | 50 mg |
| Polyvinylpyrrolidone (mean molecular weight 25,000) | 170 mg |
| Polyethylene glycol (mean molecular weight 4,000) | 14 mg |
| Hydroxypropylmethylcellulose | 40 mg |
| Talc | 4 mg |
| Magnesium stearate | 2 mg |

The active compound is moistened with a 10% strength aqueous solution of the polyvinylpyrrolidone and the mixture is forced through a sieve of 1.0 mm mesh width and is dried at 50° C. The granules thus obtained are mixed with polyethylene glycol (mean molecular weight 4,000), hydroxypropylmethylcellulose, talc and magnesium stearate and the mixture is pressed to give tablets each weighing 280 mg.

| 4. Example of dragees | |
|---|---|
| An active compound of the formula I | 60 mg |
| Lactose | 90 mg |
| Corn starch | 60 mg |
| Polyvinylpyrrolidone | 6 mg |
| Magnesium stearate | 1 mg |

The mixture of the active compound with lactose and corn starch is moistened with an 8% strength aqueous solution of the polyvinylpyrrolidone and granulated by passing through a 1.5 mm sieve; the granules are dried at 50° C. and forced through a 1.0 mm sieve. The granules obtained after this operation are mixed with magnesium stearate and the mixture is pressed to form dragee cores. These are coated in a conventional manner with a shell which essentially consists of sugar and talc.

| 5. Capsule formulation | |
|---|---|
| An active compound of the formula I | 5 mg |
| Magnesium stearate | 2.0 mg |
| Lactose | 19.3 mg |

| 6. Injection solution | |
|---|---|
| An active compound of the formula I | 10 mg |
| Sodium chloride | 9 mg |

-continued

Distilled water, q.s. to make 1.0 ml

We claim:
1. A 10-substituted 5-cyanomethylene-dibenzo[a,d]-cycloheptene of the formula I

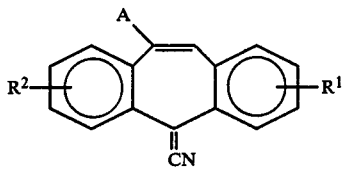

where $R^1$ and $R^2$ are hydrogen, halogen, alkyl of 1 to 3 carbon atoms or trifluoromethyl, and A is an amino radical —$NR^4R^5$, where $R^4$ and $R^5$ together with the nitrogen atom by which they are linked form a piperidine, piperazine or homopiperazine ring, the second nitrogen atom where present being unsubstituted or substituted by alkyl of 1 to 3 carbon atoms, hydroxyalkyl of 2 or 3 carbon atoms, alkoxyalkyl, the alkoxy and alkyl radical each being of 1 to 3 carbon atoms, cycloalkyl or cycloalkylmethyl, of 3 to 7 carbon atoms in the cycloalkyl ring, or alkynyl of 2 to 5 carbon atoms, and may be further substituted by oxygen in the form of an N-oxide, its pure cis-isomer and trans-isomer, and its physiologically tolerated addition salts with acids.

2. A compound of the formula I as set forth in claim 1, where $R^1$ and $R^2$ are hydrogen, fluorine, chlorine, methyl or trifluoromethyl and where A, is piperidine, piperazine or homopiperazine, which may be substituted at the ring carbon atoms by methyl or hydroxyl and in which the second ring nitrogen, where present, is substituted by methyl, ethyl, β-hydroxyethyl, cyclopropyl or propynyl and may be in the form of the N-oxide.

3. A compound of the formula I as claimed in claim 1, where $R^1$ and $R^2$ are hydrogen or chlorine, and A, as an amino radical

is 4-methyl-piperazin-1-yl, 4-ethyl-piperazin-1-yl, 4-methyl-4-oxy-piperazin-1-yl or N'-methyl-homopiperazin-1-yl.

4. A compound of the formula I as set forth in claim 1, wherein $R^1$ and $R^2$ are hydrogen or chlorine and where A is piperidine, piperazine or homopiperazine, and in which the second ring nitrogen, where present, is substituted by methyl, ethyl, β-hydroxyethyl and may be in the form of the N-oxide.

5. cis,trans-5-Cyanomethylene-10-(4-methyl-piperazin-1-yl)-dibenzo[a,d]-cycloheptene.
6. cis-5-Cyanomethylene-10-(4-methyl-piperazin-1-yl)-dibenzo[a,d]-cycloheptene.
7. trans-5-Cyanomethylene-10-(4-(methyl-piperazin-1-yl)-dibenzo[a,d]-cycloheptene.
8. cis,trans-5-Cyanomethylene-10-(4-methyl-4-oxy-piperazin-1-yl)-dibenzo[a,d]-cycloheptene.
9. cis-trans-5-Cyanomethylene-2-chloro-10-(4-methyl-piperazin-1-yl)-dibenzo[a,d]-cycloheptene.
10. cis-5-Cyanomethylene-2-chloro-10-(4-methyl-piperazin-1-yl)-dibenzo[a,d]-cycloheptene.
11. trans-5-Cyanomethylene-2-chloro-10-(4-methyl-piperazin-1-yl)-dibenzo[a,d]-cycloheptene.
12. cis,trans-5-Cyanomethylene-10-(4-ethyl-piperazin-1-yl)-dibenzo[a,d]-cycloheptene.
13. cis-5-Cyanomethylene-10-(4-ethyl-piperazin-1-yl)-dibenzo[a,d]-cycloheptene.
14. trans-5-Cyanomethylene-10-(4-ethyl-piperazin-1-yl)-dibenzo[a,d]-cycloheptene.
15. cis-trans-5-Cyanomethylene-10-(N'-methyl-homopiperazin-1-yl)-dibenzo[a,d]-cycloheptene.

* * * * *